(12) United States Patent
Song

(10) Patent No.: US 11,703,060 B1
(45) Date of Patent: Jul. 18, 2023

(54) NECK-HANGING FAN

(71) Applicant: Xuefeng Song, Shenzhen (CN)

(72) Inventor: Xuefeng Song, Shenzhen (CN)

(\*) Notice: Subject to any disclaimer, the term of this patent is extended or adjusted under 35 U.S.C. 154(b) by 0 days.

(21) Appl. No.: 18/167,924

(22) Filed: Feb. 13, 2023

(30) Foreign Application Priority Data

Jan. 5, 2023 (CN) .......................... 202320048472.9

(51) Int. Cl.
| | |
|---|---|
| *F04D 25/06* | (2006.01) |
| *F04D 29/42* | (2006.01) |
| *F04D 29/62* | (2006.01) |
| *F04D 17/16* | (2006.01) |
| *F04D 29/44* | (2006.01) |
| *F04D 25/08* | (2006.01) |
| *F04D 29/28* | (2006.01) |
| *F04D 25/16* | (2006.01) |
| *A41D 20/00* | (2006.01) |
| *A61F 7/02* | (2006.01) |
| *A41D 13/002* | (2006.01) |
| *F04D 29/00* | (2006.01) |
| *A61F 7/00* | (2006.01) |

(52) U.S. Cl.
CPC ..... *F04D 25/0673* (2013.01); *A41D 13/0025* (2013.01); *A41D 20/005* (2013.01); *A61F 7/02* (2013.01); *F04D 17/16* (2013.01); *F04D 25/08* (2013.01); *F04D 25/084* (2013.01); *F04D 25/166* (2013.01); *F04D 29/005* (2013.01); *F04D 29/281* (2013.01); *F04D 29/424* (2013.01); *F04D 29/4226* (2013.01); *F04D 29/4246* (2013.01); *F04D 29/441* (2013.01); *F04D 29/626* (2013.01); *A61F 2007/0011* (2013.01); *F24F 2221/12* (2013.01); *F24F 2221/38* (2013.01)

(58) Field of Classification Search
CPC .............. F04D 25/084; F04D 25/0673; F04D 29/4246; F04D 25/166; F04D 17/16; F04D 29/424; F04D 29/441; F04D 29/281; F04D 25/08; F04D 29/005; F04D 29/4226; F04D 29/626; A61F 2007/0011; A61F 7/02; A41D 13/0025; A41D 20/005; F24F 2221/38; F24F 2221/12
See application file for complete search history.

(56) References Cited

U.S. PATENT DOCUMENTS

| | | | | |
|---|---|---|---|---|
| 10,578,119 | B2* | 3/2020 | Lee | .................... A41D 20/005 |
| 10,709,601 | B2* | 7/2020 | Adair | ...................... A61F 7/02 |
| 11,187,241 | B1* | 11/2021 | Liu | ...................... F04D 29/441 |

(Continued)

*Primary Examiner* — Peter J Bertheaud
(74) *Attorney, Agent, or Firm* — Jeenam Park

(57) ABSTRACT

A neck-hanging fan, comprises a housing that can be worn on the neck and a fan assembly, wherein the two extended tail ends of the housing are provided with an accommodating chamber, and an air duct communicating with the accommodating chamber is formed in the housing, a fan assembly is arranged in the accommodating chamber, an air inlet hole communicating with the accommodating chamber is arranged on the housing, and a plurality of air outlet holes communicating with the air duct are arranged on the outer wall of the housing, and the plurality of air outlet holes are distributed along the extension direction of the air duct. The end of the air outlet away from the fan assembly is provided with a wind gathering plate extending into the air duct, wherein a plurality of wind gathering plates are provided.

13 Claims, 8 Drawing Sheets

(56) References Cited

U.S. PATENT DOCUMENTS

| | | | |
|---|---|---|---|
| 11,319,960 B2* | 5/2022 | Liu | .................. F04D 29/282 |
| 2020/0187574 A1* | 6/2020 | Te Hsiang | ......... A41D 13/0053 |
| 2021/0355959 A1 | 11/2021 | Liu | |
| 2022/0106963 A1* | 4/2022 | Li | .................. F04D 29/4246 |
| 2022/0235785 A1* | 7/2022 | Li | .................. F04D 25/084 |

* cited by examiner

NECK-HANGING FAN
>
> ## CROSS-REFERENCE TO RELATED APPLICATIONS
>
> This is a U.S. patent application which claims the priority and benefit of Chinese Patent Application Number 202320048472.9, filed on Jan. 5, 2023, the disclosure of which is incorporated herein by reference in its entirety.
>
> ## TECHNICAL FIELD
>
> The present application relates to the technical field of fans, in particular to a neck-hanging fan.
>
> ## BACKGROUND
>
> The neck-hanging fan is a blowing device that can be worn on the user's neck. It can move with the user and release the user's hands. By blowing air to the face and neck of the human body, the purpose of cooling and heat dissipation can be achieved.
>
> The neck-hanging fan generally comprises a housing that can be worn on the neck and a fan assembly. An air duct is arranged in the housing, and an air outlet is provided on the outer wall of the housing. The fan assembly sucks external air into the air duct and then discharges it from the air outlet. However, the existing neck-hanging fan has a small air volume near the air outlet of the fan assembly, and the wind force is small, uneven, and the blowing effect is not good.
>
> ## SUMMARY
>
> Aiming at the deficiencies in the prior art, the present application provides a neck-hanging fan, which can increase the air output volume, the wind force, and the blowing effect of the air outlet hole close to the fan assembly.
>
> In order to achieve the above object, this application adopts the following technical solutions:
>
> A neck-hanging fan, comprises a housing that can be worn on the neck and a fan assembly, wherein the two extended tail ends of the housing are provided with an accommodating chamber, and an air duct communicating with the accommodating chamber is formed in the housing, a fan assembly is arranged in the accommodating chamber, an air inlet hole communicating with the accommodating chamber is arranged on the housing, and a plurality of air outlet holes communicating with the air duct are arranged on the outer wall of the housing, and the plurality of air outlet holes are distributed along the extension direction of the air duct, wherein the end of the air outlet away from the fan assembly is provided with a wind gathering plate extending into the air duct, wherein a plurality of wind gathering plates are provided, and the protruding heights of the plurality of wind gathering plates along an air supply direction of the air duct gradually decrease. By arranging the wind gathering plate extending into the air duct at the end of the air outlet away from the fan assembly, and providing a plurality of the wind gathering plates, the protruding heights of the plurality of wind gathering plates along an air supply direction of the air duct gradually decrease, the fan assembly sucks the outside air into the accommodating chamber and delivers the air in the accommodating chamber to the air duct. When the air flows along the air supply direction of the air duct, the air in the air duct is led to the air outlet hole by utilizing the wind gathering effect of the wind gathering plate. The higher the protruding height of the wind gathering plate, the more obvious the wind gathering effect, so that the air outlet close to the fan assembly has a large air volume, strong wind force and better blowing effect.
>
> As a preferred solution, the wind gathering plate separates two adjacent air outlet holes from each other.
>
> As a preferred solution, a baffle is arranged inside the housing, the air duct is formed between the upper surface of the baffle and the inner side wall of the housing, and the height of the air duct decreases gradually along the air supply direction.
>
> As a preferred solution, the air outlet holes are arranged in strip shape, and the length direction of the air outlet holes is the same as the extending direction of the air duct.
>
> As a preferred solution, the wind gathering plate extends obliquely from the inner side wall of the housing toward the direction of approaching the fan assembly.
>
> As a preferred solution, an included angle between the inner walls of the housing of the wind gathering plate facing the side wall of the fan assembly is 30°-40°.
>
> As a preferred solution, the width of the wind gathering plate perpendicular to the air supply direction is greater than the width of the air outlet holes perpendicular to the air supply direction.
>
> As a preferred solution, the housing comprises a first housing, a second housing and a connecting part, one end of the first housing and the second housing are connected through the connecting part, and the accommodating chamber and the air duct are formed in the first housing and the second housing, and the outer walls of the first housing and the second housing are provided with the air inlet holes and the air outlet holes.
>
> As a preferred solution, a channel is formed in the connecting part, one end of the channel communicates with the air duct in the first housing, and the other end of the channel communicates with the air duct in the second housing, and the outer wall of the connecting part is formed with a plurality of blowing through holes communicated with the channel.
>
> As a preferred solution, the fan assembly comprises an impeller and a motor that drives the impeller to rotate, a mounting groove is formed in the first housing and the second housing, and a battery is provided in the mounting groove, and the motor is electrically connected to the battery.
>
> As a preferred solution, the side of the first housing facing the second housing is provided with a wire slot, one end of the wire slot communicates with the adjacent accommodating chamber, and the other end of the wire slot communicates with the adjacent mounting groove.
>
> As a preferred solution, the side of the first housing away from the second housing is provided with a first connecting cover, and a button switch is provided on the first connecting cover, and a PCB board is also provided in the mounting groove in the first housing, the button switch is electrically connected to the PCB board.
>
> As a preferred solution, a first gap communicating with the accommodating chamber is formed between the peripheral edge of the first connecting cover and the first housing.
>
> Compared with the prior art, the present application has obvious advantages and beneficial effects, specifically, by arranging the wind gathering plate extending into the air duct at the end of the air outlet away from the fan assembly, and providing a plurality of the wind gathering plates, the protruding heights of the plurality of wind gathering plates along an air supply direction of the air duct gradually decrease, the fan assembly sucks the outside air into the accommodating chamber and delivers the air in the accommodating chamber to the air duct. When the air flows along the air supply direction of the air duct, the air in the air duct is led to the air outlet hole by utilizing the wind gathering effect of the wind gathering plate. The higher the protruding height of the wind gathering plate, the more obvious the wind gathering effect, so that the air outlet close to the fan assembly has a large air volume, strong wind force and better blowing effect.

In order to more clearly illustrate the structural features, technical means and the specific purpose and functions achieved by the application, the application will be further described in detail in conjunction with the accompanying drawings and specific embodiments below:

REFERENCE SIGNS

Figure 1:
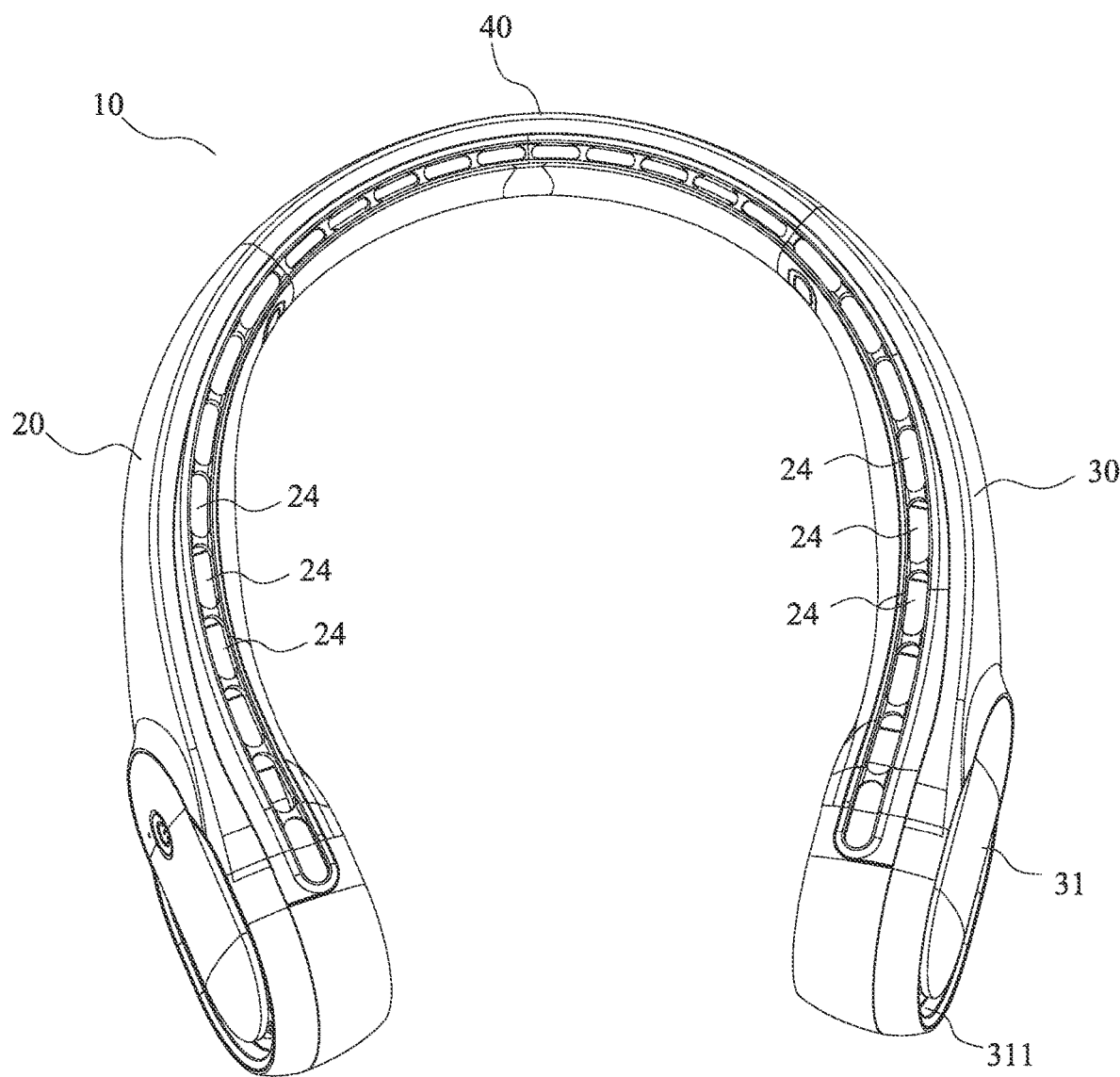
FIG. 1 is a structural diagram of the embodiment of the present application in the assembled state.
Figure 2:
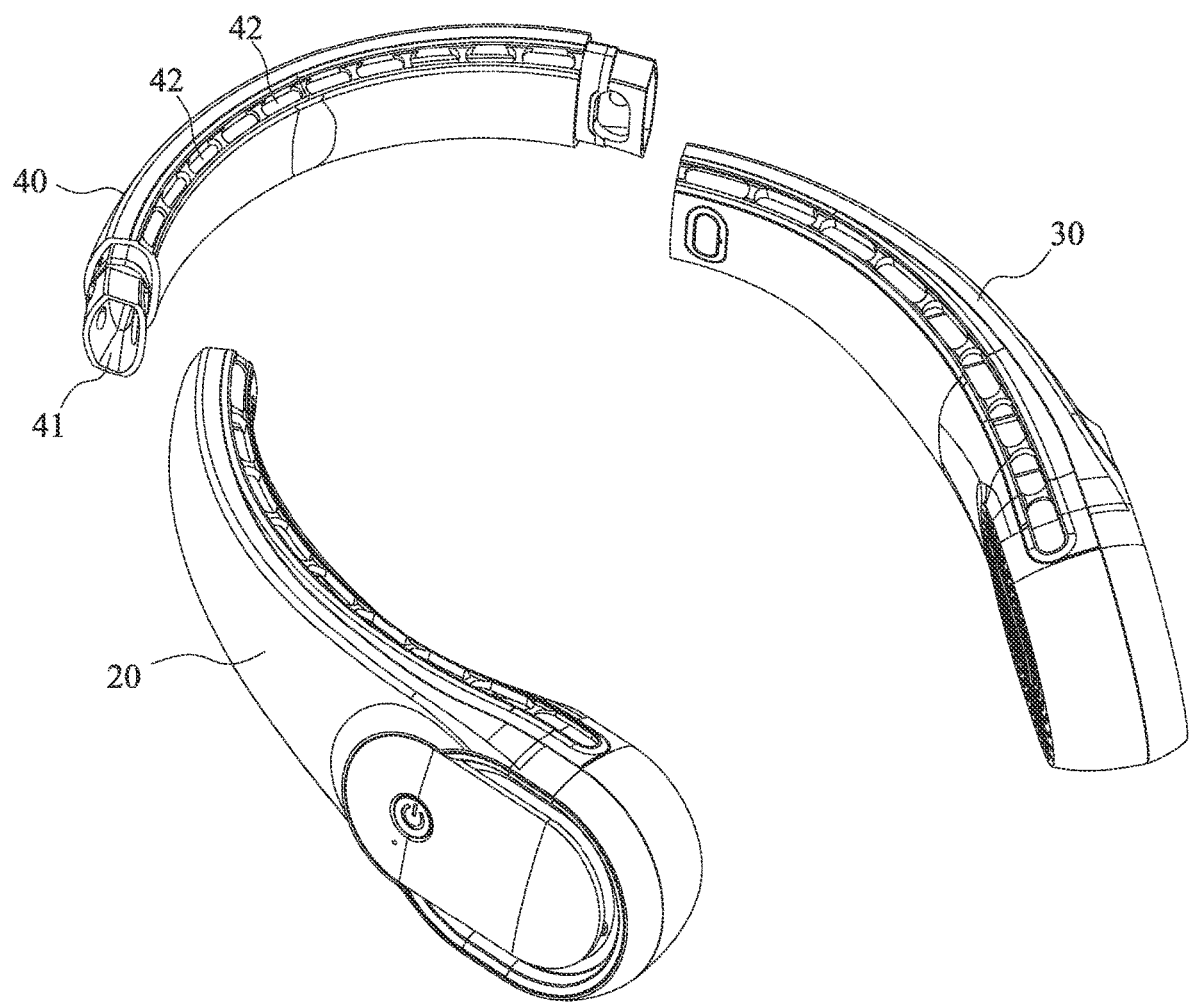
FIG. 2 is an exploded schematic diagram of the embodiment of the present application.
Figure 3:
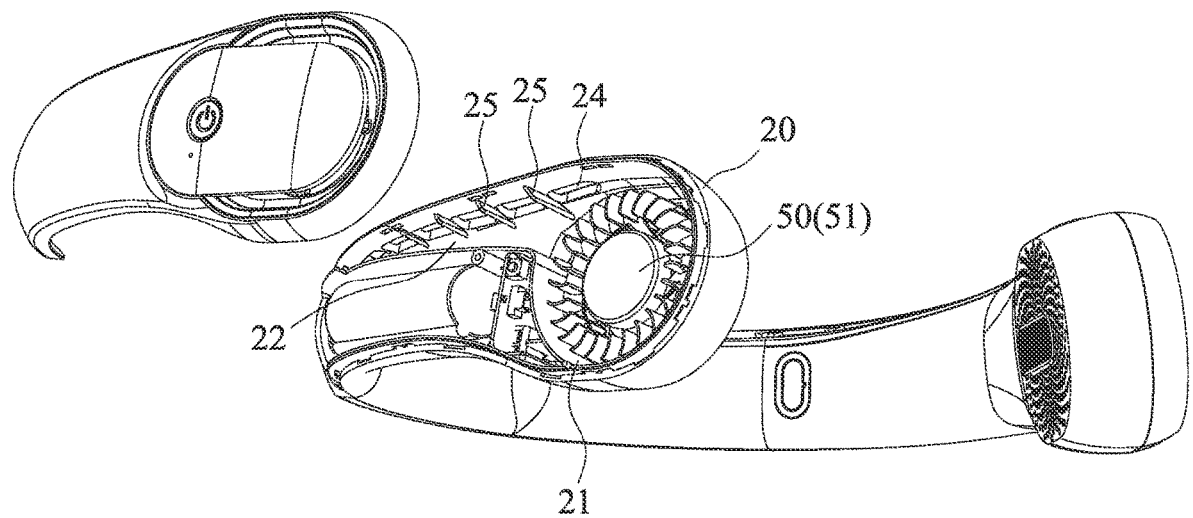
FIG. 3 is an exploded schematic diagram of another perspective of an embodiment of the present application.
Figure 4:
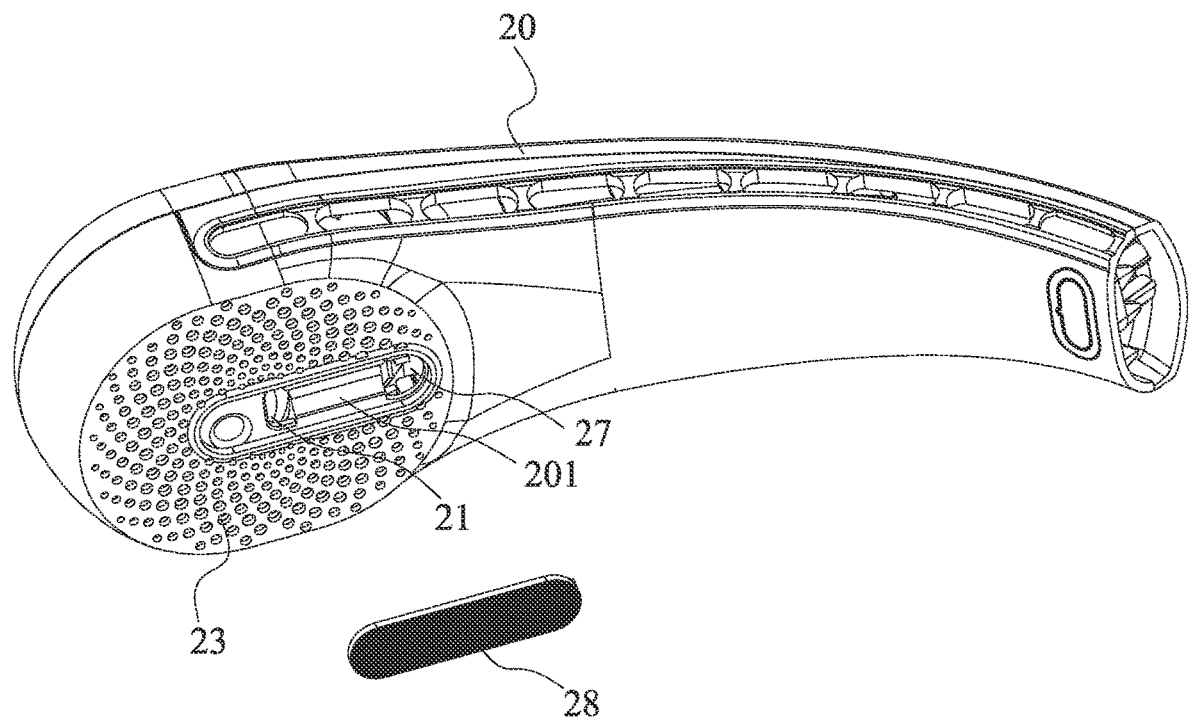
FIG. 4 is an exploded schematic diagram of the first housing of the embodiment of the present application.
Figure 5:
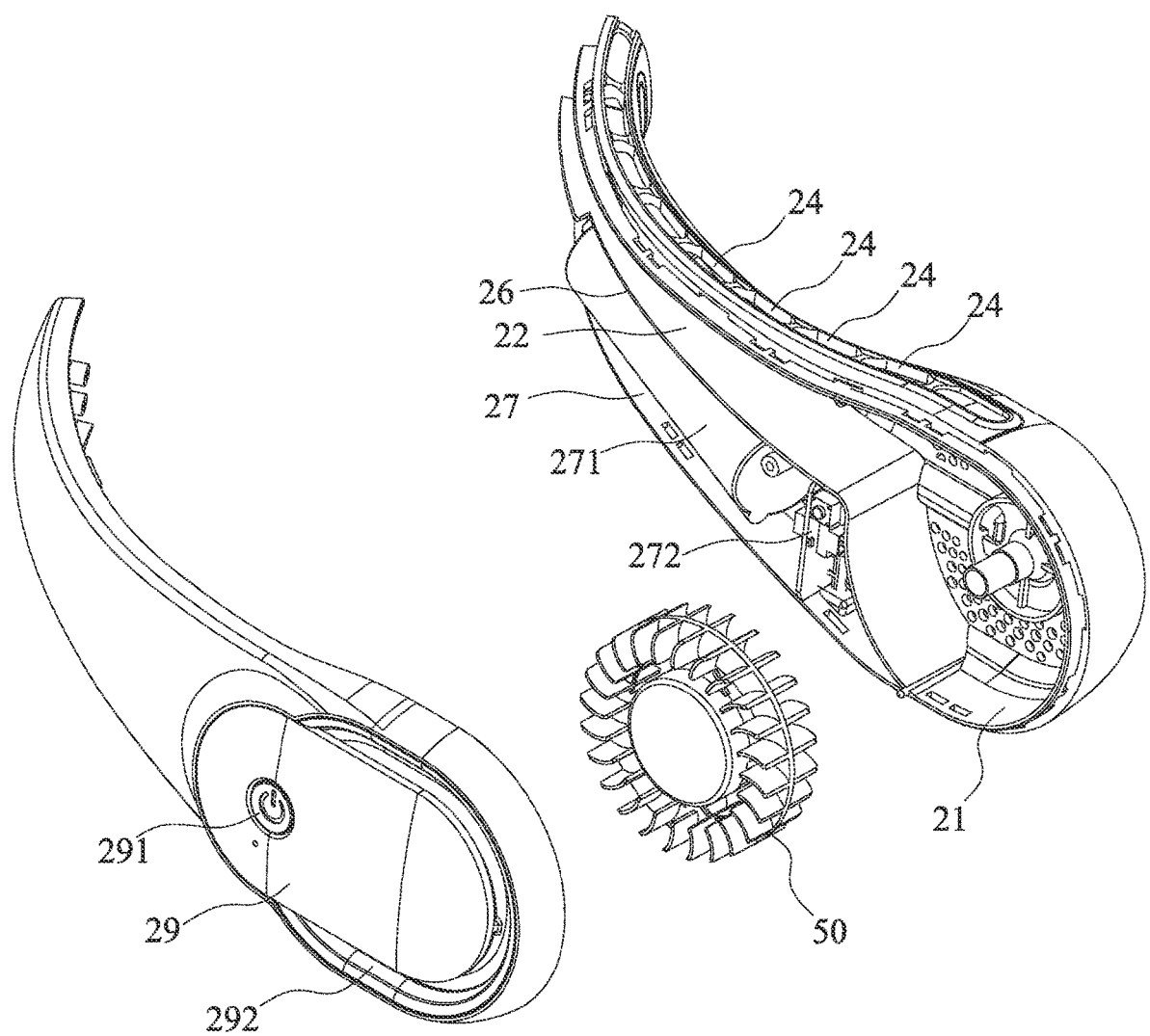
FIG. 5 is an exploded schematic diagram of the first housing of the embodiment of the present application from another perspective.

10—Housing 20—First housing 21—Accommodating chamber
22—Air duct 23—Air inlet hole 24—Air outlet hole
25—Wind gathering plate 26—Baffle 27—Mounting groove
271—Battery 272—PCB board 28—Cover plate
29—First connecting cover 291—Button switch 292—First gap
30—Second housing 31—Second connecting cover 311—Second gap
40—Connecting part 41—Channel 42—Blowing through hole
50—Fan assembly 51—Impeller

DETAILED DESCRIPTION

In the description of the present application, it should be noted that the terms "center", "upper", "lower", "left", "right", "vertical", "horizontal", "inner", "outer", etc. which are used to indicate position or positional relationship are based on the position or positional relationship shown in the drawings, and are only for the convenience of describing the application and simplifying the description, rather than indicating or implying that the indicated position or element must have a specific orientation and be constructed in a specific orientation and operation, therefore cannot be understood as a limitation of the present application.

In the description of the present application, it should be noted that unless otherwise clearly specified and limited, the terms "installation", and "connection" should be understood in a broad sense, for example, it can be a fixed connection or a detachable connection, or integrally connected; it can be a mechanical connection or an electrical connection; it can be directly connected, or indirectly connected through an intermediate medium, and it can be the internal communication between two components. For those skilled in the art, the specific meaning of the above-mentioned terms in the present application can be understood according to the specific circumstances.

As shown in FIGS. 1-8, the present application discloses a neck-hanging fan, comprising a housing 10 that can be worn on the neck and a fan assembly 50, wherein the two extended tail ends of the housing 10 are provided with an accommodating chamber 21, the fan assembly 50 is arranged in the accommodating chamber 21, and an air duct 22 communicating with the accommodating chamber 21 is formed in the housing 10, the air duct 22 is arranged along the extending direction of the housing 10. An air inlet hole 23 communicating with the accommodating chamber 21 is arranged on the housing 10, a plurality of air outlet holes 24 communicating with the air duct 22 are arranged on the outer wall of the housing 10, and the plurality of air outlet holes 24 are distributed along the extension direction of the air duct 22. The air outlet holes 24 are arranged in strip shape, and the length direction of the air outlet holes 24 is the same as the extending direction of the air duct 22. The end of the air outlet 24 away from the fan assembly 50 is provided with a wind gathering plate 252 extending into the air duct, wherein a plurality of wind gathering plates 25 are provided, and the protruding heights of the plurality of wind gathering plates 25 along an air supply direction of the air duct 22 gradually decrease. The wind gathering plate 25 separates two adjacent air outlet holes 24 from each other. The two adjacent air outlet holes 24 are separated from each other by arranging the wind gathering plate 25, so as to avoid air crosstalk between two adjacent air outlet holes 24 and improve the uniformity and stability of the air outlet.

It should be noted that, in this application, a wind gathering plate 25 can be arranged between two adjacent air outlet holes 24, or a wind gathering plate 25 can be arranged between a plurality of air outlet holes 24.

It should also be noted that the air outlet 24 away from the fan assembly 50 can be selectively provided with the wind gathering plate 25 according to the size of the air outlet 24 and the magnitude of the wind force.

Figure 6:
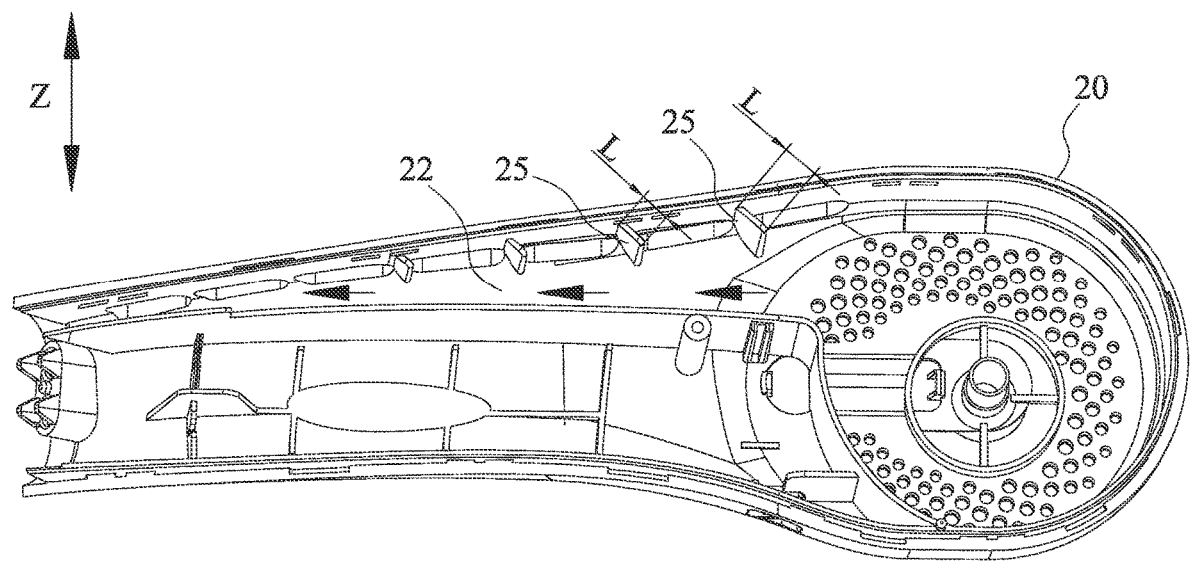
FIG. 6 is a schematic diagram of the internal structure of the first housing in the first viewing angle of the embodiment of the present application.
Figure 7:
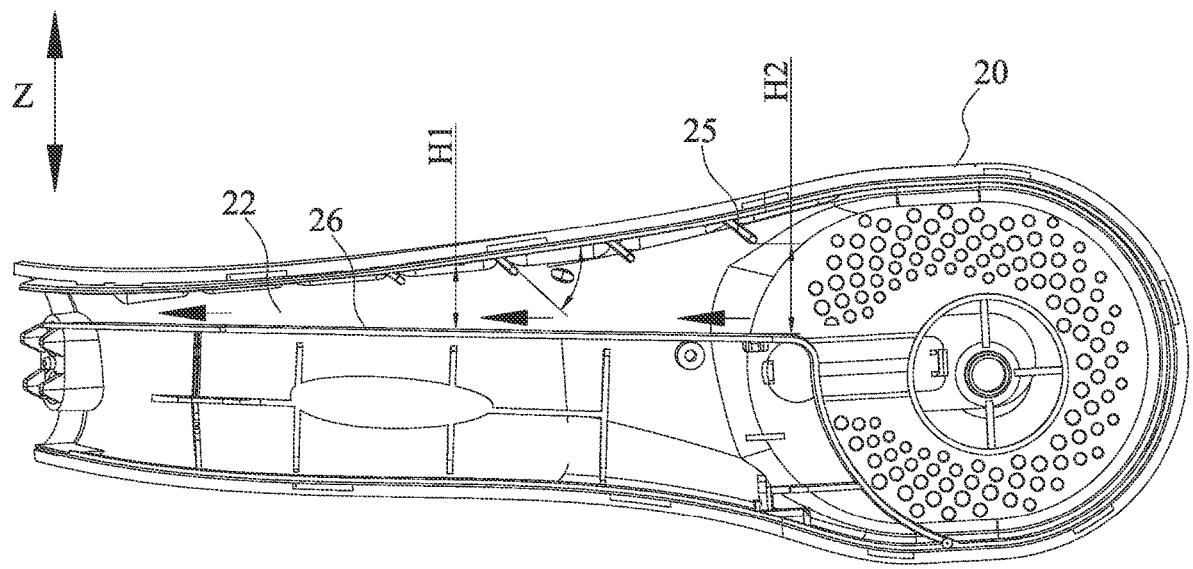
FIG. 7 is a schematic diagram of the internal structure of the first housing in the second viewing angle of the embodiment of the present application.
Figure 8:
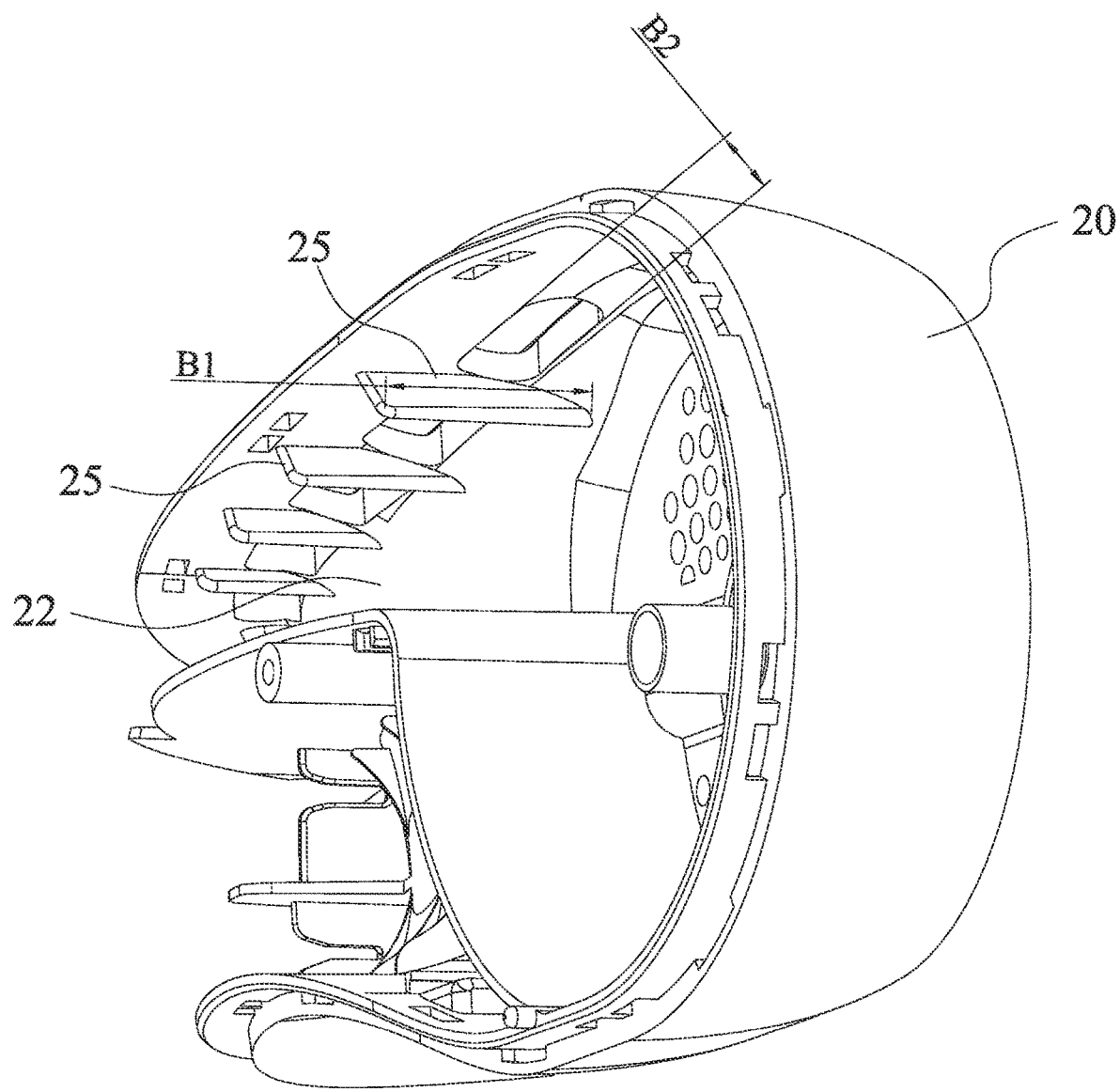
FIG. 8 is a schematic diagram of the internal structure of the first housing in the third viewing angle of the embodiment of the present application.

A baffle 26 is arranged inside the housing 10, the air duct 22 is formed between the upper surface of the baffle 26 and the inner side wall of the housing 10, and the height H1 of the air duct 22 decreases gradually along the air supply direction. For the convenience of understanding and description, Z in FIGS. 6 and 7 represents the up and down direction. In this application, the height of the air duct along the air supply direction is defined as the distance between the upper surface of the baffle and the inner side wall of the upper end of the housing 10. The distance H2 between the plurality of wind gathering plates 25 and the baffle 26 along the air supply direction of the air duct 22 decreases gradually. By gradually reducing the distance H2 between the wind gathering plate 25 and the baffle 26 along the air supply direction of the air duct 22, the air output and the wind force of the air outlet near the fan assembly can be increased.

The wind gathering plate 25 extends obliquely from the inner side wall of the housing 10 toward the direction of approaching the fan assembly 50. An included angle θ between the inner walls of the housing 10 of the wind gathering plate 25 facing the side wall of the fan assembly 50 is 30°-40°, preferably 35°.

The width of the wind gathering plate 25 perpendicular to the air supply direction is greater than the width of the air outlet holes 24 perpendicular to the air supply direction, and the width of the plurality of wind gathering plates 25 gradually decreases along the air supply direction of the air duct 22.

The housing 10 comprises a first housing 20, a second housing 30 and a connecting part 40, the connecting part 40 is arranged in an arc shape, and the connecting part 40 is arranged in a cylindrical shape, one end of the first housing 20 and the second housing 30 are connected through the connecting part 40, and the accommodating chamber 21 and the air duct 22 are formed in the first housing 20 and the second housing 30, and the outer walls of the first housing 20 and the second housing 30 are provided with the air inlet holes 23 and the air outlet holes 24. The air inlet hole 23 on the first housing 20 is arranged on the side of the first housing 20 facing the second housing 30, and the air inlet hole 23 on the second housing 30 is arranged on the side of the second housing 30 facing the first housing 20.

A channel 41 is formed in the connecting part 40, one end of the channel 41 communicates with the air duct 22 in the first housing 20, and the other end of the channel 41 communicates with the air duct 22 in the second housing 30, and the outer wall of the connecting part 40 is formed with a plurality of blowing through holes 42 communicated with the channel 41. The air blowing through hole 42 and the air outlet hole 24 are located on the same side of the housing 10.

The fan assembly 50 comprises an impeller 51 and a motor that drives the impeller 51 to rotate, a mounting groove 27 is formed in the first housing 20 and the second housing 30, and a battery 281 is provided in the mounting groove 27, and the motor is electrically connected to the battery 281.

The side of the first housing 20 facing the second housing 30 is provided with a wire slot, one end of the wire slot communicates with the adjacent accommodating chamber 21, and the other end of the wire slot communicates with the adjacent mounting groove 27. A cover plate 28 is provided at the opening of the wire slot. By providing the wire slot, it is convenient to arrange the wires between the motor and the battery 281 in the wire slot, so that the wires avoid the air duct 22 and prevent the wires from affecting the air flow in the air duct 22.

The side of the first housing 20 away from the second housing 30 is provided with a first connecting cover 29, and a button switch 291 is provided on the first connecting cover 29, and a PCB board 272 is also provided in the mounting groove 27 in the first housing 20, the button switch 291, the motor and the battery 281 are electrically connected to the PCB board. a first gap 292 communicating with the accommodating chamber 21 is formed between the peripheral edge of the first connecting cover 29 and the first housing 20. During air intake, air can enter the accommodating chamber 21 from the first gap 292. It can be understood that the side of the second housing 30 far away from the first housing 20 is provided with a second connecting cover 31, and a second gab 311 is formed between the peripheral edge of the second connecting cover 31 and the second housing 30, the second gap 311 communicates with the accommodating chamber 21 in the second housing 30.

The working principle of this application: press the button switch 291, the motor drives the impeller 51 to rotate, and the impeller 51 rotates so that the air enters the accommodating chamber 21 from the air inlet 23. The impeller 51 rotates so that the air in the accommodating chamber 21 is discharged into the air duct 22, a part of the air in the air duct 22 is directed to the air outlet hole 24 through the wind gathering plate 25 and is discharged from the air outlet hole 24, and another part of the air in the air duct 22 enters the channel 41 and is discharged from the blowing through hole 42.

To sum up, in the present application, by arranging the wind gathering plate 25 extending into the air duct 22 at the end of the air outlet 24 away from the fan assembly 50, and providing a plurality of the wind gathering plates 25, the protruding heights of the plurality of wind gathering plates 25 along an air supply direction of the air duct 22 gradually decrease, the fan assembly 50 sucks the outside air into the accommodating chamber 21 and delivers the air in the accommodating chamber 21 to the air duct 22. When the air flows along the air supply direction of the air duct 22, the air in the air duct 22 is led to the air outlet hole 24 by utilizing the wind gathering effect of the wind gathering plate 25. The higher the protruding height of the wind gathering plate 25, the more obvious the wind gathering effect, so that the air outlet 24 close to the fan assembly 50 has a large air volume, a strong wind force, and a better blowing effect.

The above are only the preferred embodiments of the present application, and are not intended to limit the present application. Therefore, any modification, equivalent replacement, improvement, etc. made to the above embodiments according to the technical practice of the present application still fall within the scope of the technical solution of the present application.

What is claimed is:

1. A neck-hanging fan, comprises a housing that can be worn on the neck and a fan assembly, wherein two extended tail ends of the housing are provided with an accommodating chamber, and an air duct communicating with the accommodating chamber is formed in the housing, a fan assembly is arranged in the accommodating chamber, an air inlet hole communicating with the accommodating chamber is arranged on the housing, and a plurality of air outlet holes communicating with the air duct are arranged on an outer wall of the housing, and the plurality of air outlet holes are distributed along the extension direction of the air duct, wherein the end of an air outlet away from the fan assembly is provided with a wind gathering plate extending into the air duct, wherein a plurality of wind gathering plates are provided, and the protruding heights of the plurality of wind gathering plates along an air supply direction of the air duct gradually decrease.

2. The neck-hanging fan according to claim 1, wherein each wind gathering plate separates two adjacent air outlet holes from each other.

3. The neck-hanging fan according to claim 1, wherein a baffle is arranged inside the housing, the air duct is formed between an upper surface of the baffle and an inner side wall of the housing, and the height of the air duct decreases gradually along the air supply direction.

4. The neck-hanging fan according to claim 1, wherein the air outlet holes are arranged in strip shape, and the length direction of the air outlet holes is the same as the extending direction of the air duct.

5. The neck-hanging fan according to claim 1, wherein each wind gathering plate extends obliquely from at least one inner side wall of the housing toward the direction of approaching the fan assembly.

6. The neck-hanging fan according to claim 5, wherein an included angle between the at least one inner side wall of the housing and each wind gathering plate is 30°-40°.

7. The neck-hanging fan according to claim 1, wherein the width of the wind gathering plate perpendicular to the air supply direction is greater than the width of the air outlet holes perpendicular to the air supply direction.

8. The neck-hanging fan according to claim 1, wherein the housing comprises a first housing, a second housing and a connecting part, one end of the first housing and the second housing are connected through the connecting part, and the accommodating chamber and the air duct are formed in the first housing and the second housing, and outer walls of the first housing and the second housing are provided with the air inlet holes and the air outlet holes.

9. The neck-hanging fan according to claim 8, wherein a channel is formed in the connecting part, one end of the channel communicates with the air duct in the first housing, and the other end of the channel communicates with the air duct in the second housing, and an outer wall of the connecting part is formed with a plurality of blowing through holes communicated with the channel.

10. The neck-hanging fan according to claim 8, wherein the fan assembly comprises an impeller and a motor that drives the impeller to rotate, a mounting groove is formed in the first housing and the second housing, and a battery is provided in the mounting groove, and the motor is electrically connected to the battery.

11. The neck-hanging fan according to claim 10, wherein a side of the first housing facing the second housing is provided with a wire slot, one end of the wire slot communicates with the adjacent accommodating chamber, and the other end of the wire slot communicates with the adjacent mounting groove.

12. The neck-hanging fan according to claim 10, wherein a side of the first housing away from the second housing is provided with a first connecting cover, and a button switch is provided on the first connecting cover, and a PCB board is also provided in the mounting groove in the first housing, the button switch is electrically connected to the PCB board.

13. The neck-hanging fan according to claim 12, wherein a first gap communicating with the accommodating chamber is formed between a peripheral edge of the first connecting cover and the first housing.

* * * * *